US010478595B2

(12) United States Patent
Kokish (10) Patent No.: US 10,478,595 B2
(45) Date of Patent: Nov. 19, 2019

(54) INFINITELY ROTATABLE TOOL WITH FINITE ROTATING DRIVE SHAFTS (71) Applicant: Auris Health, Inc., Redwood City, CA (US)

(72) Inventor: Arkady Kokish, Los Gatos, CA (US)

(73) Assignee: Auris Health, Inc., Redwood City, CA (US)

( * ) Notice: Subject to any disclaimer, the term of this patent is extended or adjusted under 35 U.S.C. 154(b) by 231 days.

(21) Appl. No.: 15/613,032

(22) Filed: Jun. 2, 2017

(65) Prior Publication Data
US 2017/0296784 A1 Oct. 19, 2017

Related U.S. Application Data (62) Division of application No. 13/788,440, filed on Mar. 7, 2013, now Pat. No. 9,668,814.

(51) Int. Cl.
*A61M 25/01* (2006.01)
*A61B 34/30* (2016.01)
*A61B 34/35* (2016.01)
*A61M 25/06* (2006.01)
*A61B 17/00* (2006.01)

(52) U.S. Cl.
CPC ......... *A61M 25/0113* (2013.01); *A61B 34/30* (2016.02); *A61B 34/35* (2016.02); *A61M 25/0147* (2013.01); *A61M 25/0662* (2013.01); *A61B 2017/00477* (2013.01); *A61B 2034/301* (2016.02); *A61M 2205/52* (2013.01); *A61M 2207/00* (2013.01); *Y10T 29/49002* (2015.01); *Y10T 74/18096* (2015.01)

(58) Field of Classification Search
CPC .............. A61B 34/30; A61B 2034/301; A61B 2034/302; A61B 2034/303; A61B 2034/304; A61B 2034/71; A61B 2034/715

See application file for complete search history.

(56) References Cited

U.S. PATENT DOCUMENTS

| | | | |
|---|---|---|---|
| 2,556,601 A | 6/1951 | Schofield |
| 2,566,183 A | 8/1951 | Forss |
| 2,730,699 A | 1/1956 | Gratian |
| 2,884,808 A | 5/1959 | Mueller |
| 3,294,183 A | 12/1966 | Riley et al. |

(Continued)

FOREIGN PATENT DOCUMENTS

| | | |
|---|---|---|
| CN | 101500470 | 8/2009 |
| CN | 102665590 | 9/2012 |

(Continued)

OTHER PUBLICATIONS

Mayo Clinic, Robotic Surgery, https://www.mayoclinic.org/tests-procedures/robotic-surgey/about/pac-20394974?p=1, downloaded from the internet on Jul. 12, 2018, 2 pp.

*Primary Examiner* — Anh T Dang
(74) *Attorney, Agent, or Firm* — Knobbe, Martens, Olson & Bear, LLP (57) ABSTRACT

A catheter rotation drive apparatus includes first and second drives that are engageable to an output shaft. When the first drive is engaged to the output shaft and rotated, the output shaft rotates in an output rotation direction, and when the second drive is engaged to the output shaft and rotated, the output shaft rotates in the output rotation direction.

14 Claims, 8 Drawing Sheets

(56) References Cited

U.S. PATENT DOCUMENTS

| | | |
|---|---|---|
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 6/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,398,691 A | 3/1995 | Martin et al. |
| 5,408,409 A | 4/1995 | Glassman et al. |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,631,973 A | 5/1997 | Green |
| 5,713,946 A | 2/1998 | Ben-Haim |
| 5,749,362 A | 5/1998 | Funda et al. |
| 5,767,840 A | 6/1998 | Selker |
| 5,779,623 A | 7/1998 | Bonnell |
| 5,792,135 A | 8/1998 | Madhani et al. |
| 5,855,583 A | 1/1999 | Wang et al. |
| 5,859,934 A | 1/1999 | Green |
| 5,876,325 A | 3/1999 | Mizuno et al. |
| 5,921,968 A | 7/1999 | Lampropoulos et al. |
| 5,951,475 A | 9/1999 | Gueziec et al. |
| 5,967,934 A | 10/1999 | Ishida et al. |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,226,543 B1 | 5/2001 | Gilboa et al. |
| 6,259,806 B1 | 7/2001 | Green |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,424,885 B1 | 7/2002 | Niemeyer et al. |
| 6,436,107 B1 | 8/2002 | Wang et al. |
| 6,487,940 B2 | 12/2002 | Hart et al. |
| 6,491,701 B2 | 12/2002 | Tierney et al. |
| 6,695,813 B1 | 2/2004 | Wollschlager |
| 6,726,675 B1* | 4/2004 | Beyar ............... A61M 25/0105 600/106 |
| 6,786,896 B1 | 9/2004 | Madhani et al. |
| 6,827,712 B2 | 12/2004 | Tovey et al. |
| 7,044,936 B2 | 5/2006 | Harding |
| 7,155,315 B2 | 12/2006 | Niemeyer et al. |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,277,417 B2 | 10/2012 | Fedinec et al. |
| 8,291,791 B2 | 10/2012 | Light et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,894,610 B2 | 11/2014 | MacNamara et al. |
| 8,961,533 B2 | 2/2015 | Stahler et al. |
| 8,968,333 B2 | 3/2015 | Yu et al. |
| 9,173,713 B2 | 11/2015 | Hart et al. |
| 9,204,933 B2 | 12/2015 | Reis et al. |
| 9,326,822 B2 | 5/2016 | Lewis et al. |
| 9,408,669 B2 | 8/2016 | Kokish et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,818,681 B2 | 3/2018 | Wallace et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,143,360 B2 | 12/2018 | Roelle et al. |
| 10,145,747 B1 | 12/2018 | Lin et al. |
| 10,159,532 B1 | 12/2018 | Ummalaneni et al. |
| 10,299,870 B2 | 5/2019 | Connolly et al. |
| 2001/0042643 A1 | 11/2001 | Krueger et al. |
| 2002/0045905 A1 | 4/2002 | Gerbi et al. |
| 2002/0098938 A1 | 7/2002 | Milboume et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2004/0015053 A1 | 1/2004 | Bieger |
| 2004/0152972 A1 | 6/2004 | Hunter |
| 2004/0243147 A1 | 12/2004 | Lipow |
| 2005/0004579 A1 | 1/2005 | Schneider et al. |
| 2005/0183532 A1 | 8/2005 | Najaf et al. |
| 2005/0222554 A1 | 10/2005 | Wallace et al. |
| 2006/0025676 A1 | 2/2006 | Viswanathan et al. |
| 2006/0111692 A1 | 5/2006 | Hlavka et al. |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0191177 A1 | 8/2007 | Nagai et al. |
| 2007/0245175 A1 | 10/2007 | Zheng et al. |
| 2007/0299427 A1 | 12/2007 | Yeung et al. |
| 2008/0039255 A1* | 2/2008 | Jinno .................. A61B 17/062 474/148 |

(56) References Cited

U.S. PATENT DOCUMENTS

| | | |
|---|---|---|
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0247944 A1 | 10/2009 | Kirschenman et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1* | 11/2011 | Yates ............... A61B 17/07207 606/170 |
| 2011/0306836 A1 | 12/2011 | Ohline et al. |
| 2012/0071695 A1 | 3/2012 | Stahler et al. |
| 2012/0071821 A1 | 3/2012 | Yu |
| 2012/0071894 A1 | 3/2012 | Tanner et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0222019 A1 | 8/2014 | Brudniok |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0157945 A1 | 6/2016 | Madhani |
| 2016/0166234 A1 | 6/2016 | Zhang |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0281049 A1 | 10/2017 | Yamamoto |
| 2017/0290631 A1 | 10/2017 | Lee et al. |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |

(56) References Cited

U.S. PATENT DOCUMENTS

2019/0142537 A1  5/2019  Covington et al.
2019/0167366 A1  6/2019  Ummalaneni

FOREIGN PATENT DOCUMENTS

| DE | 19649082 | 1/1998 |
|---|---|---|
| DE | 102004020465 | 9/2005 |
| EP | 1 442 720 | 8/2004 |
| EP | 2 567 670 | 3/2013 |
| EP | 3 025 630 | 6/2016 |
| JP | 2009-139187 | 6/2009 |
| JP | 2010-046384 | 3/2010 |
| WO | WO 02/074178 | 9/2002 |
| WO | WO 03/086190 | 10/2003 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/0151993 | 9/2017 |

\* cited by examiner

FIG. 8

INFINITELY ROTATABLE TOOL WITH FINITE ROTATING DRIVE SHAFTS

This application is a divisional of U.S. patent application Ser. No. 13/788,440, filed Mar. 7, 2013, the entirety of which is hereby incorporated by reference in its entirety for all purposes.

BACKGROUND

Robotic interventional systems and devices are well suited for performing minimally invasive medical procedures as opposed to conventional techniques wherein the patient's body cavity is open to permit the surgeon's hands access to internal organs. Advances in technology have led to significant changes in the field of medical surgery such that less invasive surgical procedures, in particular, minimally invasive surgery (MIS), are increasingly popular.

A MIS is generally defined as a procedure that is performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

MIS apparatus and techniques have advanced to the point where an elongated catheter instrument is controllable by selectively operating tensioning control elements within the catheter instrument. In one example, four opposing directional control elements wind their way to the distal end of the catheter which, when selectively placed in and out of tension, cause the distal end to steerably maneuver within the patient. Control motors are coupled to each of the directional control elements so that they may be individually controlled and the steering effectuated via the operation of the motors in unison.

However, in some clinical situations, it is not possible to use an elongate instrument with multi directional control elements. For instance, in some MIS procedures a microcatheter is used that does not have any steering element. Elongate instruments having multiple driving elements are typically larger in diameter and sometimes cannot pass through the naturally occurring lumens within the body (e.g., veins or arteries). In these MIS procedures, navigation can be performed with a much simpler non-steerable pre-curved catheter. These catheters can be navigated by simply rotating the pre-curved tip, while feeding the catheter into the lumen.

Robotic systems that are designed with directional control often have limited capability to rotate the entire elongate instrument. It is not necessary to rotate the entire instrument because there is complete direction control at the tip by selectively placing the directional control elements in and out of tension. However, if non deflectable instruments are attached to these robotic systems, greater rotational capability of the entire device is needed. If multiple control motors are present in a robot system that is typically used for steering a steerable catheter, it can be inconvenient or not possible to switch out the multiple motor control system, and enable it to use the simpler non-steerable device to provide catheter rotation capability.

As such, there is a need for a robotic system that can activate the directional control elements when steerable devices are attached to it and can also be used to rotate the entire device when non steerable devices are attached to it.

SUMMARY

A catheter rotation drive apparatus includes first and second drives that are engageable to an output shaft. When the first drive is engaged to the output shaft and rotated, the output shaft rotates in an output rotation direction, and when the second drive is engaged to the output shaft and rotated, the output shaft rotates in the output rotation direction.

A method of fabricating a rotatable catheter includes providing first and second drive shafts that are engageable to an output shaft, wherein when the first drive shaft is engaged to the output shaft and rotated, the output shaft rotates in an output rotation direction, and when the second drive shaft is engaged to the output shaft and rotated, the output shaft rotates in the output rotation direction.

A robotically controlled surgical system includes a robotic instrument driver, wherein the robotic instrument driver is controllable by an operator workstation. The robotic instrument driver includes a rotatable output shaft extending from a housing, and a plurality of input drives within the housing that are each rotatable about respective drive axes and coupled to rotatable shafts of the robotic instrument driver. When a first of the input drives is coupled with the output shaft, and when the first input drive is rotated, the output shaft is caused to rotate in an output rotational direction, and when a second of the input drives is coupled with the output shaft, and when the second input drive is rotated, the output shaft is caused to rotate in an output rotational direction.

BRIEF DESCRIPTION

DETAILED DESCRIPTION

Figure 1:
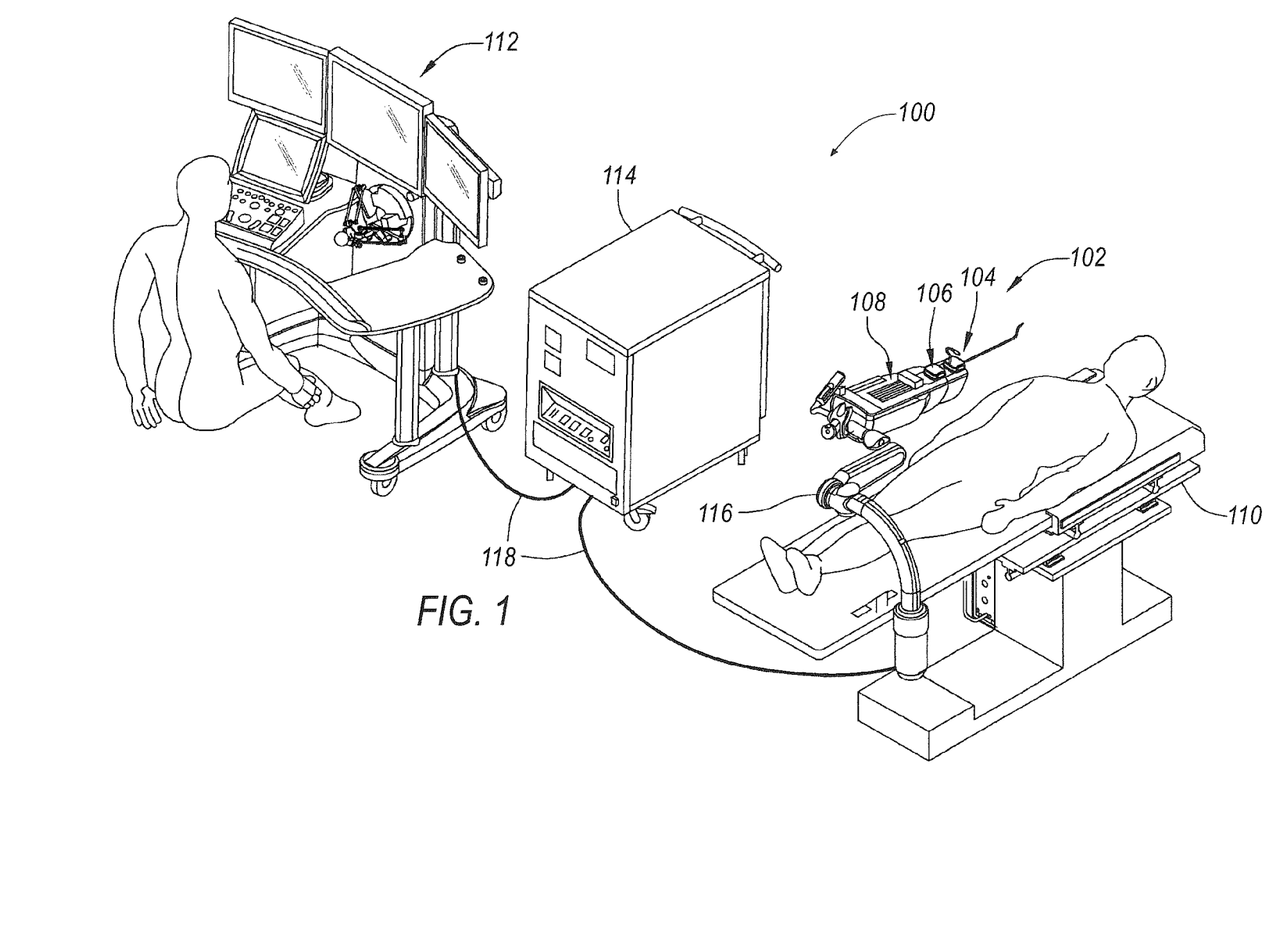
FIG. 1 is an illustration of a robotically controlled surgical system, according to one exemplary illustration.

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter" or "catheter instrument"). Catheter assembly 102 is controllable using a robotic instrument driver 108 (generally referred to as "instrument driver"). During use, a patient is positioned on an operating table or surgical bed 110 (generally referred to as "operating table") to which robotic instrument driver 108 is coupled or mounted. In the illustrated example, system 100 includes an operator workstation 112, an electronics rack 114 and associated bedside electronics box (not shown), a setup joint mounting brace 116, and instrument driver 108. A surgeon is seated at operator workstation 112 and can monitor the surgical procedure, patient vitals, and control one or more catheter devices.

System components may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

Figure 2:
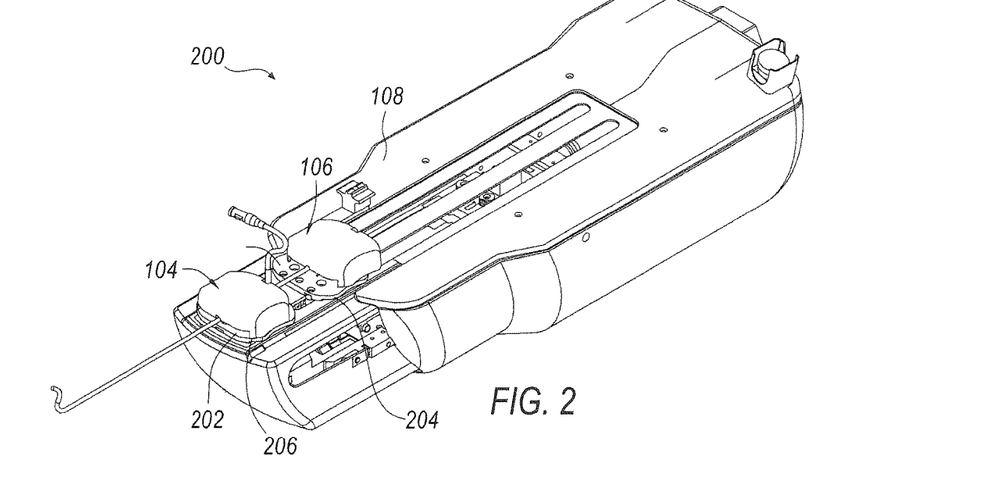
FIG. 2 is an illustration of an exemplary catheter assembly of the surgical system of FIG. 1.

Referring now to FIG. 2, an instrument assembly 200 includes sheath instrument 104 and the associated guide or catheter instrument 106 mounted to mounting plates 202, 204 on a top portion of instrument driver 108. During use, catheter instrument 106 is inserted within a central lumen of sheath instrument 104 such that instruments 104, 106 are arranged in a coaxial manner. Although instruments 104, 106 are arranged coaxially, movement of each instrument 104, 106 can be controlled and manipulated independently. For this purpose, motors within instrument driver 108 are controlled such that carriages coupled to mounting plates 204, 206 are driven forwards and backwards on bearings. As a result, a catheter coupled to guide catheter instrument 106 and sheath instrument 104 can be controllably manipulated while inserted into the patient, as will be further illustrated. Additional instrument driver 108 motors may be activated to control bending of the catheter as well as the orientation of the distal tips thereof, including tools mounted at the distal tip. Sheath catheter instrument 106 is configured to move forward and backward for effecting an axial motion of the catheter, e.g., to insert and withdraw the catheter from a patient, respectively.

Figure 3:
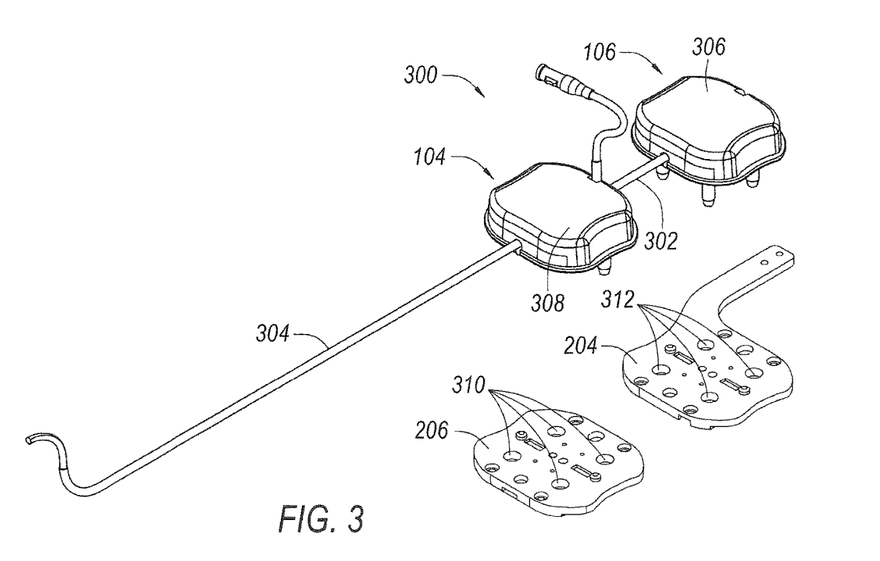
FIGS. 3 and 4 are illustrations of components of the catheter assembly of FIG. 2.

Referring to FIG. 3, an assembly 300 includes sheath instrument 104 and guide or catheter instrument 106 positioned over their respective mounting plates 206, 204. In the illustrated example, a guide catheter instrument member 302 is coaxially interfaced with a sheath catheter member 304 by inserting the guide catheter instrument member 302 into a working lumen of sheath catheter member 304. Sheath catheter member 304 includes a distal end that is manipulable via assembly 300, as will be further discussed in FIG. 5. Sheath instrument 104 and guide or catheter instrument 106 are coaxially disposed for mounting onto instrument driver 108. However, it is contemplated that a sheath instrument 108 is used without guide or catheter instrument 106, or guide or catheter instrument 106 is used without sheath instrument 104 and may be mounted onto instrument driver 108 individually.

When a catheter is prepared for use with an instrument, its splayer is mounted onto its appropriate interface plate. In this case, sheath splayer 308 is placed onto sheath interface plate 206 and a guide splayer 306 is placed onto guide interface plate 204. In the illustrated example, each interface plate 204, 206 has respectively four openings 310, 312 that are designed to receive corresponding drive shafts 314, 316 (FIG. 4 illustrates an underside perspective view of shafts 314, 316) attached to and extending from the pulley assemblies of the splayers 308, 306).

Figure 5:
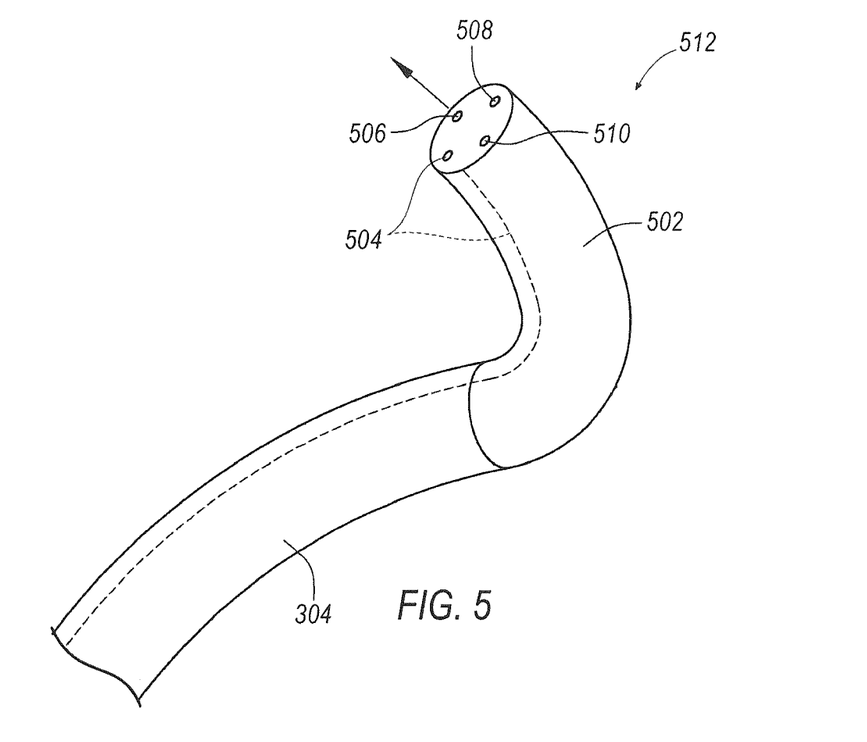
FIG. 5 illustrates a distal end of an exemplary catheter that is controllable by internal control elements.

Operator workstation 112 may include a computer monitor to display a three dimensional object, such as a catheter instrument 502 as illustrated in FIG. 5. Catheter instrument 502 may be displayed within or relative to a three dimensional space, such as a body cavity or organ, e.g., a chamber of a patient's heart. In one example, an operator uses a computer mouse to move a control point around the display to control the position of catheter instrument 502.

Figure 4:
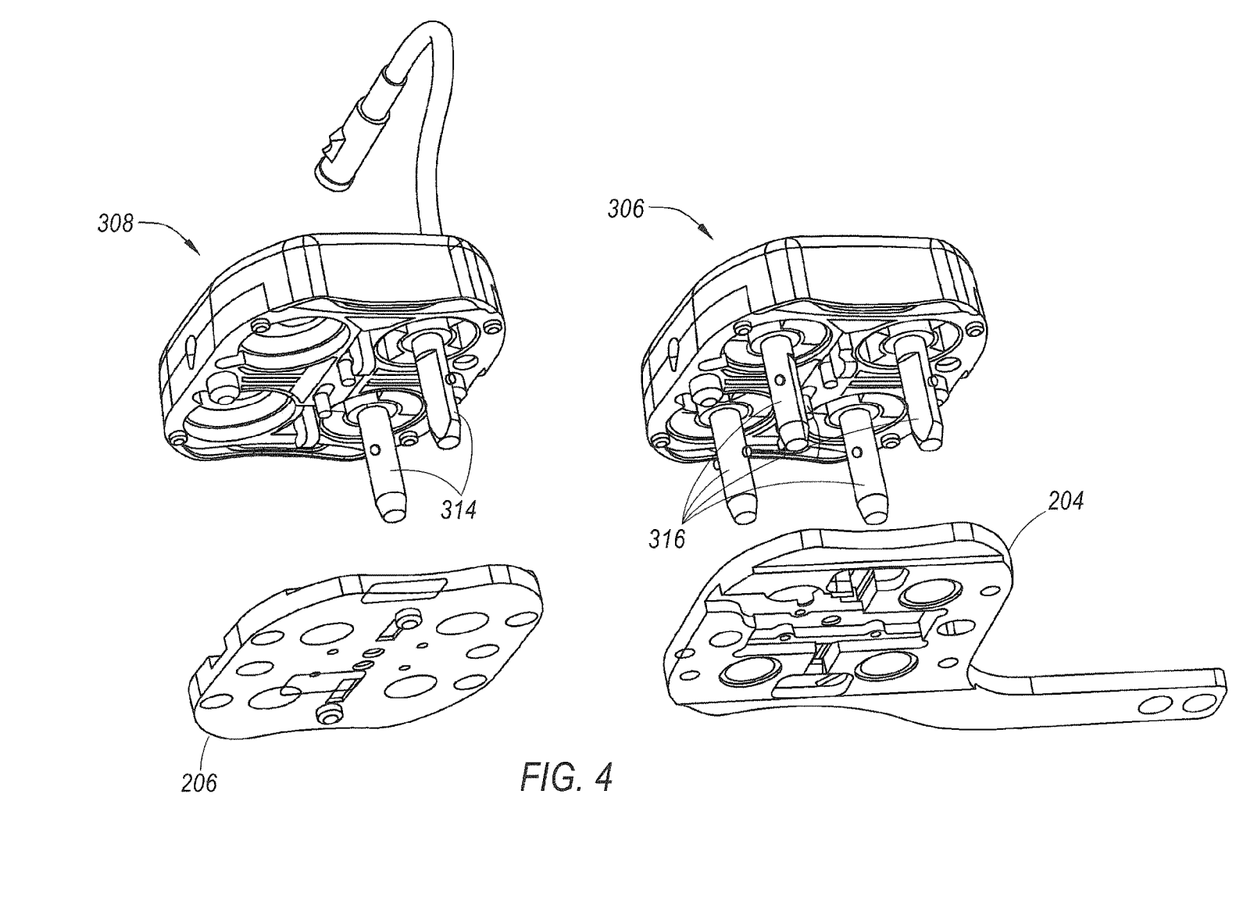

Turning now to FIGS. 3 and 4, an exemplary sheath instrument 104 and catheter instrument 106 are described in further detail. According to one exemplary illustration, sheath instrument 104 may include a sheath splayer 308 having drive shafts 314. Catheter instrument 106 may include a guide splayer 306 having drive shafts 316. Drive shafts 316 are each coupled to a respective motor within instrument driver 108 (motors not shown). When 4-wire catheter 304 is coupled to instrument driver 108, each drive shaft 316 thereof is thereby coupled to a respective wire 504-510 (see FIG. 5). As such, a distal end 512 of catheter 304 can be articulated and steered by selectively tightening and loosening wires 504-510. Typically, the amount of loosening and tightening is slight, relative to the overall length of catheter 304. That is, each wire 504-510 typically need not be tightened or loosened more than perhaps a few centimeters. As such, the motors that tighten/loosen each wire typically do not rotate more than, for example, ¾ of a rotation.

Splayer 314 and drive shaft 316 have pin/screw combinations and flats and. These features act as a key and match with corresponding features in the output shafts of the robotic system. The robotic system presents its output shaft in a fixed orientation upon boot up to receive the keyed pins of the splayer. A typical motor and gear box in a robotic system includes a hard stop in a gear box that allows the motor to find a home point every time the system is booted up. The encoder can then index from this point and position the keyed output shafts at any desired location. It is beneficial for the output shafts of the robotic system to rotate less than one full revolution, which enables a hard stop to be designed into the rotation mechanism.

Returning now to the challenge of using this robotic system to rotate a non steerable catheter. Because microcatheters are generally not torsionally stiff, and because of their relatively long length, the minimal rotations on the output shafts is generally not adequate to provide the rotational motion needed at a distal end thereof.

Figure 6A:
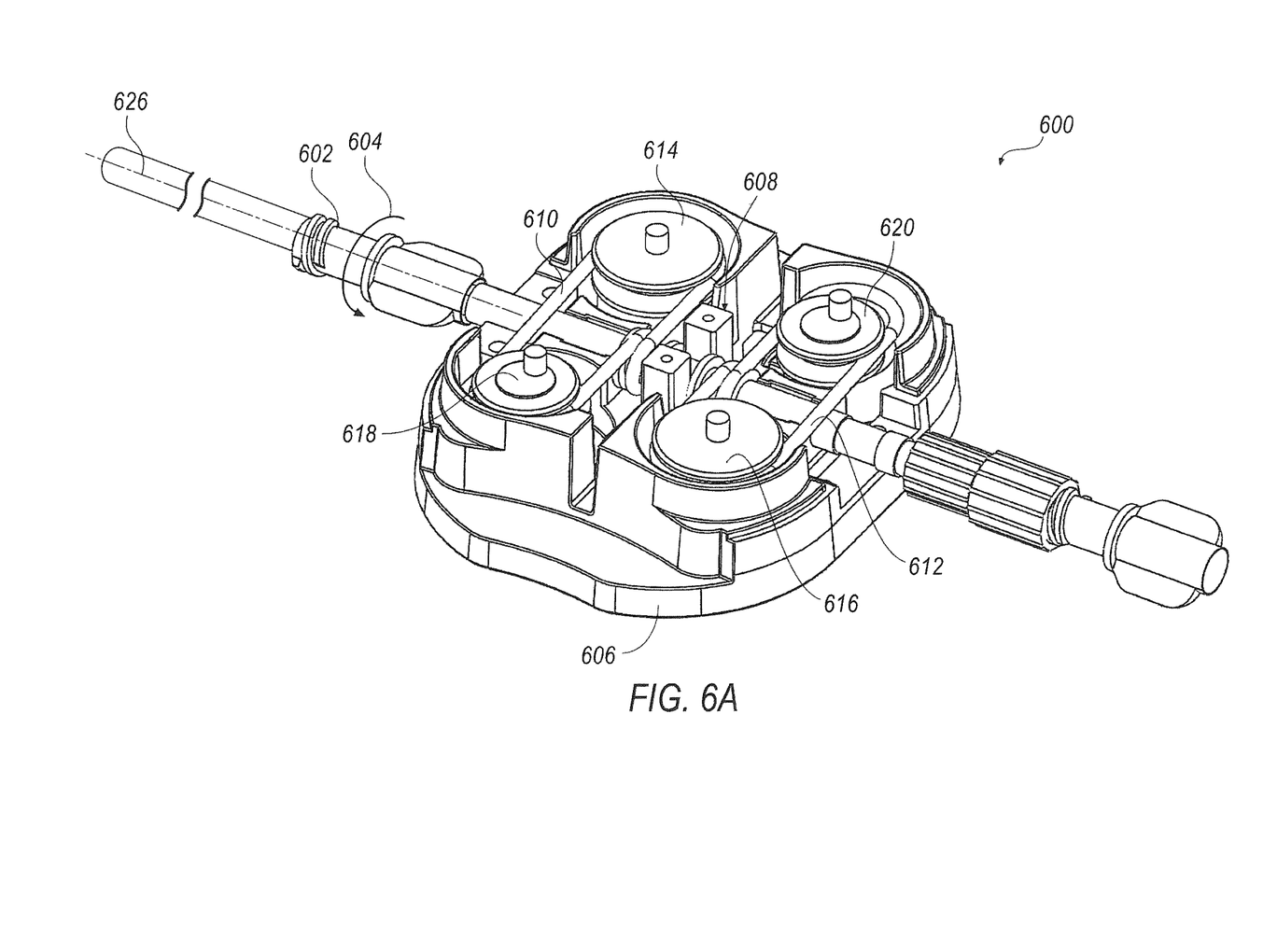
FIGS. 6A and 6B illustrate an exemplary catheter rotation device or drive apparatus.
Figure 6B:
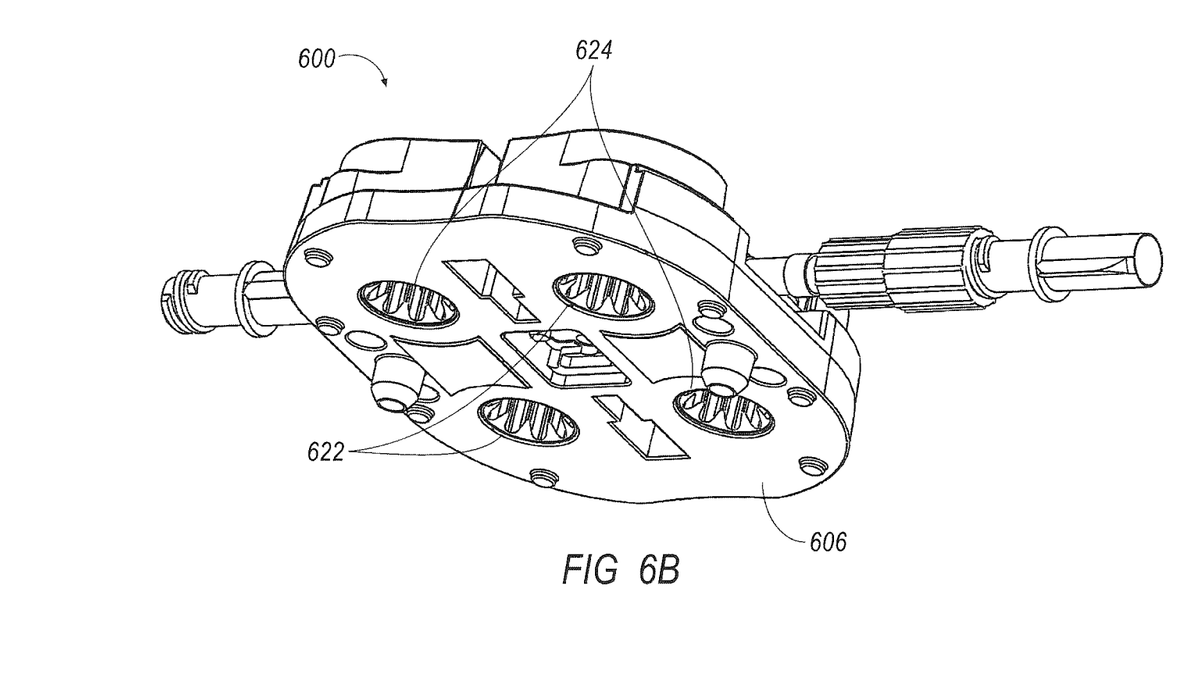

Referring to FIGS. 6A and 6B, an exemplary catheter rotation device or drive apparatus 600 is illustrated. Device 600 is an exemplary catheter instrument 106 that is positionable on instrument driver 108. Device 600 includes an output shaft 602 that is infinitely rotational in an output rotational circumferential direction 604, using the motors that tighten/loosen each wire. In one exemplary illustration, infinite rotational motion can be imparted even though the motors rotate through approximately ¾ of a rotation each. Output shaft 602 extends through a body or support structure 606, and output shaft 602 is supported via, in the example illustrated, at least one bearing 608. Bearing 608 allows free rotation of output shaft 602 relative to support structure 606. Output shaft 602 is rotationally driven in output direction 604 through a first belt or O-ring 610 and a second belt or O-ring 612. Device 600 includes a first drive pulley 614 about which first O-ring 610 is wrapped, and a second drive pulley 616 about which second O-ring 612 is wrapped. Device 600 also includes a first engagement or eccentric shaft or shaft with a cam surface 618 about which first O-ring 610 is wrapped, and a second engagement or eccentric shaft or shaft with a cam surface 620 about which second O-ring 616 is wrapped. The first and second engagement or eccentric shafts 618, 620 enable engagement of drive pulleys to drive output shaft 602, as will be further described.

As stated, drive pulleys 614, 616 and eccentric shafts 618, 620 are mechanically coupled to drive shafts, such as drive shafts 316 as shown in guide splayer 306. Incidentally, although drive shafts 316 are shown extending into guide splayer 306 in FIGS. 3 and 4, it is contemplated and understood that drive shafts 316 may instead be inserted into and remain in sheath instrument 108. As such, referring to FIG. 6B, drive shafts 316 are insertable into input shaft drives 622 and into input eccentric drives 624. Input shaft drives 622 are rotatable about respective drive axes that are approximately parallel to one another, and input drive shafts 622, as illustrated, are approximately orthogonal to a rotational axis 626 about which output rotational circumferential direction 604 rotates. Eccentric shafts 618, 620 are selectively engaged and disengaged (or unengaged) such that when one is engaged and tightens its O-ring, at the same time the other eccentric shaft is disengaged (or unengaged) and its O-ring is loose. That is, a drive pulley may be coupled to shaft 602 with its eccentric shaft engaged, while the other drive pulley may be decoupled from shaft 602 with its eccentric shaft disengaged.

Figure 7:
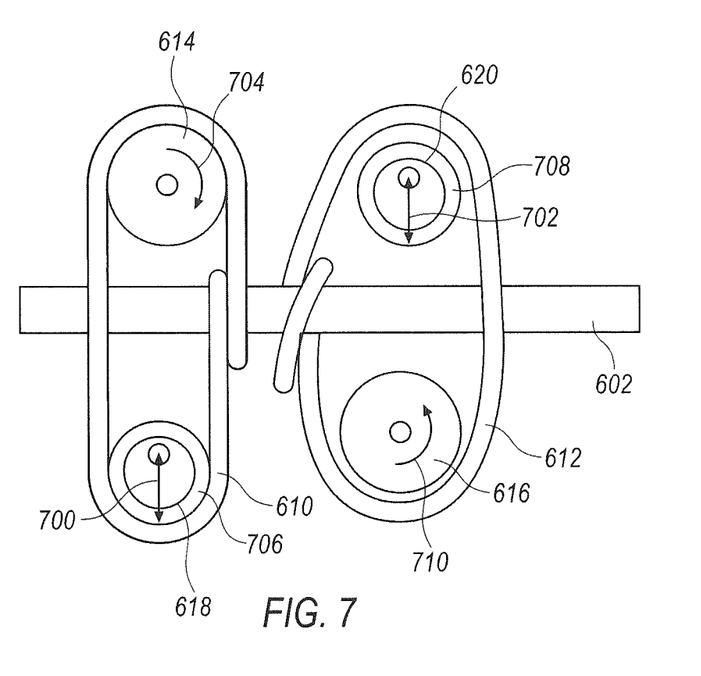
FIG. 7 illustrates a plan view showing the engagement and disengagement of drive shafts via eccentric shaft operation, according to one exemplary approach.

FIG. 7 illustrates a plan view showing the engagement and disengagement of drive shafts via eccentric shaft operation, according to an exemplary illustration. In FIG. 7, eccentric shaft 618 is shown in its rotated/engaged position such that its major eccentric dimension 700 is located away from shaft 602. With eccentric shaft 618 located accordingly, first O-ring 610 is thereby tightened about shaft 602 and also about drive pulley 614. The length of O-ring 610 is designed such that when the eccentric shaft creates the longest path for the O-ring, the O-ring is tight. At the same time, eccentric shaft 620 is in its rotated/dis-engaged position such that its major eccentric dimension 702 is located toward shaft 602. With eccentric shaft 620 located accordingly, second O-ring 612 is thereby loosened about shaft 602 and also about drive pulley 616. Under this arrangement, drive pulley 614 is caused to rotate, in this embodiment, ¾ of a turn in one direction 704 (which in one example is the rotational angular capability of drive pulley 614 and also of other rotational elements 616, 618, 620 driven by drive shafts 316). This causes shaft 602 to rotate via first O-ring 610 and about a rotational axis that is approximately orthogonal to a rotation axis of drive pulley 614. O-ring 610 also is driven relative to eccentric shaft 618 via a first wheel 706 (that is, first wheel 706 rotates relative to eccentric shaft 618).

Because eccentric shaft 620 is disengaged, rotation of output shaft 602 will not frictionally affect second O-ring 612. Further, because each drive pulley 614, 616 is rotatable about a limited rotational angle (¾ of a rotation in this example), while drive pulley 614 is causing O-ring 610 to engage and rotate output shaft 602, the other drive pulley 616 is retracting back through its retraction rotation angle 710.

After completion of the illustrated arrangement of FIG. 7, the process is reversed. That is, after drive pulley 614 reaches the end of its angular travel 704, and after drive pulley 616 has retracted back through its angular travel 710, then both eccentric shafts 618, 620 are reversed from the arrangement shown in FIG. 7 such that O-ring 610 is loose and O-ring 612 is tight. As such, drive pulley 616 is then caused to rotate in a drive angular direction that is opposite that of retraction direction 710, causing output shaft 602 to rotate in the same angular direction as that in the previous steps, and while wheel 708 is driven relative to eccentric shaft 620. Likewise, while drive shaft 616 is rotating (and causing output shaft 602 to rotate), the other drive pulley 614 is caused to retract in its direction opposite that shown as 704. In such fashion, the rotation sequence is repeated back and forth between drive pulleys and eccentric shafts such that output shaft 602 is rotated in the same angular direction for each step in the process. Likewise, it is contemplated that the entire operation can be reversed if rotation in the opposite direction is commanded by the user. The output shaft may also be caused to rotate in the other angular direction than that shown as angular direction 604 in FIG. 6A, depending on when the eccentric shafts are engaged and the angle of rotation of their respective drive pulleys. Thus, drive shaft 602 may be rotated in one angular direction during one set of conditions (i.e., engagement of each eccentric shaft and each drive pulley) or drive shaft 602 may be rotated in the opposite angular direction during an opposite set of conditions. Accordingly, infinite rotational motion (that is, repeated output rotation in one desired rotational direction) may be imparted by the drive pulleys 614, 616 in both directions even though neither pulley 614, 616 rotates even one full 360 rotation about its associated drive shaft.

Output shaft 602 may be coupled to a catheter. As stated, in a catheter that does not have steering wires such as in catheter 304 described earlier, a catheter without steering wires such as catheter 622 illustrated in FIG. 6A may be rotated infinitely in output direction 604 or in a direction opposite to output direction 604. Further, although the operation of driving one drive shaft and retracting the other drive shaft is described as occurring at essentially the same time, it is contemplated that the operation may be sequential instead. That is, the steps may be sequentially performed such that the drive shaft is driven during a first time period, and the other drive shaft is retracted during a second and subsequent time period. In other words, the two operations of driving one shaft and retracting the other need not be simultaneous.

In addition, it is contemplated that the operation of driving and retracting each drive shaft may be controlled such that the rotation of output shaft is not only infinite, but continuous as well. That is, a controller may be configured to operate one of the drive shafts at a first speed, and retraction of the other may be at a second and faster speed. In such fashion the retraction of the drive shaft may be timed so that it is next ready to drive the drive shaft when the other drive shaft reaches its limit of rotational travel.

Figure 8:
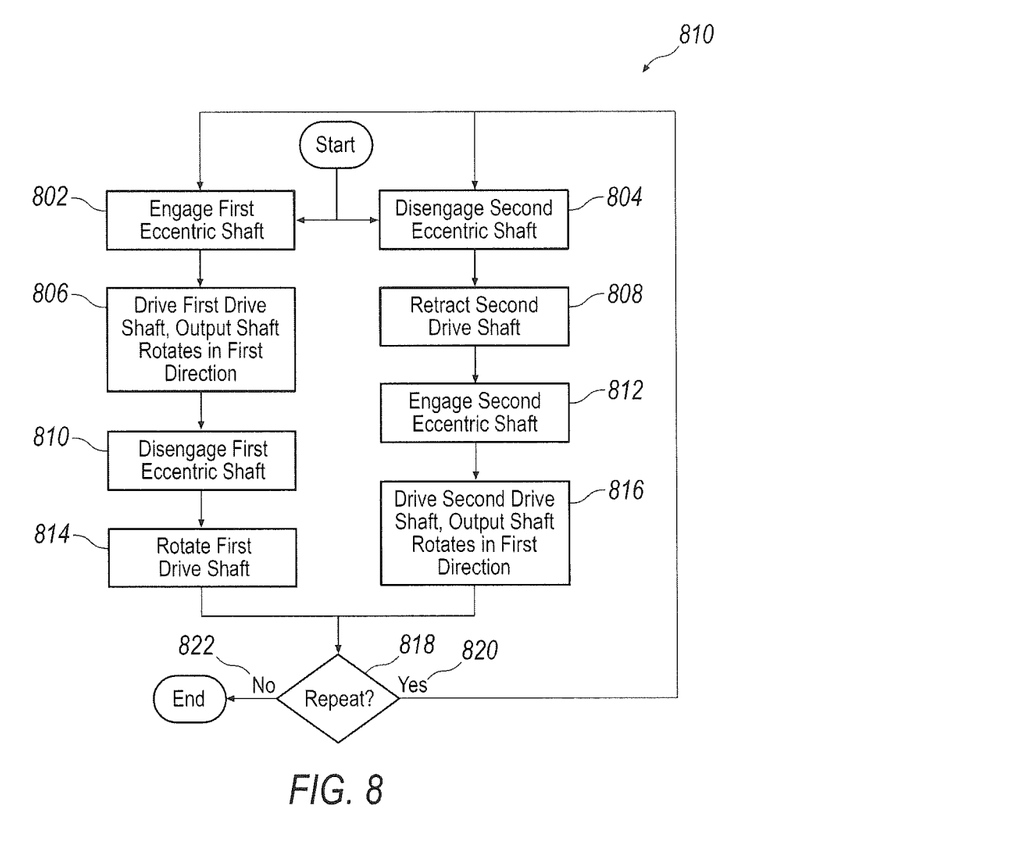
FIG. 8 illustrates a process flow diagram for an exemplary method for operating drive shafts and eccentric shafts.

Turning now to FIG. 8, a process flow diagram of an exemplary method of using a catheter is illustrated. After starting, first eccentric shaft 618 is engaged at block 802 and second eccentric shaft 620 is disengaged at block 804. While first eccentric shaft 618 is engaged, first drive shaft 614 is driven, causing output shaft 602 to rotate in a first direction, such as direction 604, at block 806. While second eccentric shaft 620 is disengaged, second drive shaft 616 is retracted at block 808. First eccentric shaft 618 is disengaged at block 810 and second eccentric shaft 620 is engaged at block 812. While second eccentric shaft 620 is engaged, second drive shaft 616 is driven, causing output shaft 602 to rotate in the first direction, such as direction 604, at block 816. While first eccentric shaft 618 is disengaged, first drive shaft 614 is retracted at block 814. At block 818, if it is desired to repeat the process 820, then process control returns to blocks 802, 804 to continue through another cycle. If not 822, the process ends.

Operator workstation 112 may include a computer or a computer readable storage medium implementing the operation of drive and implementing process 800. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A catheter rotation drive apparatus, comprising:
a first pair of input drives coupled to one another via a first belt, the first pair of input drives comprising a first drive and a first engagement shaft, the first drive coupled to a first drive pulley;
a second pair of input drives coupled to one another via a second belt, the second pair of input drives comprising a second drive and a second engagement shaft, the second drive coupled to a second drive pulley;
wherein each of the first and second drives are engageable to an output shaft;
wherein when the first drive is engaged to the output shaft and rotated, the output shaft rotates in an output rotation direction,
wherein when the second drive is engaged to the output shaft and rotated, the output shaft rotates in the output rotation direction,
wherein when the first engagement shaft of the first pair of input drives is engaged, the second engagement shaft of the second pair of input drives is disengaged, such that when the first drive pulley is rotated in its drive direction, the output shaft is caused to rotate via the first belt in the output rotational direction.

2. The catheter rotation drive apparatus of claim 1, wherein each of the plurality of input drives are rotatable about respective drive axes that are approximately parallel with one another, and wherein the drive axes are approximately orthogonal to a rotational axis of the output shaft that defines the output rotational direction.

3. The catheter rotation drive apparatus of claim 1, wherein when the engagement shaft of the second pair is disengaged, the second drive pulley is rotated in a retraction direction that is opposite its drive direction.

4. The catheter rotation drive apparatus of claim 1, wherein when the engagement shaft of the first pair is disengaged, the engagement shaft of the second pair is engaged, such that when the second drive pulley is rotated in its drive direction, the output shaft is caused to rotate in the output rotational direction.

5. The catheter rotation drive apparatus of claim 1, wherein an overall output shaft rotation is greater than an input rotation of either of the first and second drives.

6. The catheter rotation drive apparatus of claim 1, wherein the engagement shafts of the first and second pairs of input drives are each eccentric shafts.

7. The catheter rotation drive apparatus of claim 1, wherein the first and second belts are O-rings.

8. The catheter rotation drive apparatus of claim 7, wherein:
  the first O-ring is wrapped about:
    the engagement shaft of the of the first pair of the input drives;
    the first drive pulley; and
    the output shaft; and
  the second O-ring is wrapped about:
    the engagement shaft of the of the second pair of the input drives;
    the second drive pulley; and
    the output shaft.

9. The catheter rotation drive apparatus of claim 1, wherein the first and second drives are each not rotatable more than one full revolution.

10. The catheter rotation drive apparatus of claim 1, wherein the output shaft is rotated in a continuously through engagement of the first drive and engagement of the second drive.

11. A method of fabricating a rotatable catheter comprising:
  providing first and second drive shafts that are engageable to an output shaft;
  wherein:
    when the first drive shaft is engaged to a first engagement shaft and to the output shaft, a second drive shaft is disengaged from a second engagement shaft and from the output shaft, and when the first drive shaft is rotated, the output shaft rotates in an output rotation direction; and
    when the second drive shaft is engaged to the second engagement shaft and to the output shaft, the first drive shaft is disengaged from the first engagement shaft and from the output shaft, and when the second drive shaft rotated, the output shaft rotates in the output rotation direction.

12. The method of claim 11, further comprising:
  wherein the first drive shaft is rotatable in a first drive angular direction to cause the output shaft to rotate in the output rotational direction.

13. The method of claim 11, further comprising:
  providing the first engagement shaft such that it is subsequently disengagable from the first drive shaft and from the output shaft via the first belt; and
  providing the second engagement shaft such that it is subsequently engagable against the second drive shaft and against the output shaft via the second belt;
  wherein the second drive shaft is rotatable in a second drive angular direction to cause the output shaft to rotate in the output rotational direction.

14. The method of claim 13, further comprising:
  providing the first drive shaft such that it is retractable in a retraction direction that is opposite its drive angular direction, when the first engagement shaft is disengaged from the first drive shaft.

* * * * *

UNITED STATES PATENT AND TRADEMARK OFFICE
CERTIFICATE OF CORRECTION

PATENT NO. : 10,478,595 B2
APPLICATION NO. : 15/613032
DATED : November 19, 2019
INVENTOR(S) : Arkady Kokish Page 1 of 2

It is certified that error appears in the above-identified patent and that said Letters Patent is hereby corrected as shown below:

On the Title Page

Column 2, Item (56), Line 2, under Other Publications, delete "surgey" and insert --surgery--.

On Page 2, Column 1, Item (56), Line 14, under U.S. Patent Documents, delete "6/1987" and insert --8/1987--.

On Page 2, Column 1, Item (56), Line 58, under U.S. Patent Documents, delete "6,695,813" and insert --6,695,818--.

On Page 2, Column 2, Item (56), Line 48, under U.S. Patent Documents, delete "Milboume" and insert --Milbourne--.

On Page 2, Column 2, Item (56), Line 57, under U.S. Patent Documents, delete "6/2004" and insert --8/2004--.

On Page 3, Column 1, Item (56), Line 35, under U.S. Patent Documents, delete "2012/0071695" and insert --2012/0071895--.

In the Specification

In Column 3, Line 67, delete "306)." and insert --306.--.

In the Claims

In Column 9, Line 30 (Approx.), Claim 8, after "of the" delete "of the".

In Column 9, Line 35 (Approx.), Claim 8, after "of the" delete "of the".

Signed and Sealed this
Third Day of March, 2020

Andrei Iancu
*Director of the United States Patent and Trademark Office*

CERTIFICATE OF CORRECTION (continued)
U.S. Pat. No. 10,478,595 B2

In Column 10, Line 28 (Approx.), Claim 13, delete "disengagable" and insert --disengageable--.

In Column 10, Line 31 (Approx.), Claim 13, delete "engagable" and insert --engageable--.